US008850903B2

(12) United States Patent
Curtis et al.

(10) Patent No.: US 8,850,903 B2
(45) Date of Patent: Oct. 7, 2014

(54) APPARATUS AND METHOD FOR ASPIRATING AND DISPENSING LIQUID

(75) Inventors: Richard H. Curtis, Gorham, ME (US);
Kirby Pilcher, Portland, ME (US);
David L. Bohnsack, New Gloucester, ME (US); Charles Ewing, Westbook, ME (US); George Rodrigues, Westbrook, ME (US); John T. Bradshaw, Gorham, ME (US); Marc Boillat, Auvernier (CH)

(73) Assignees: Artel, Inc., Westbrook, ME (US);
Seyonic S.A., Neuchatel (CH)

( * ) Notice: Subject to any disclaimer, the term of this patent is extended or adjusted under 35 U.S.C. 154(b) by 832 days.

(21) Appl. No.: 13/005,965

(22) Filed: Jan. 13, 2011

(65) Prior Publication Data
US 2011/0126645 A1 Jun. 2, 2011

Related U.S. Application Data

(62) Division of application No. 11/684,182, filed on Mar. 9, 2007, now Pat. No. 7,870,797.

(60) Provisional application No. 60/788,849, filed on Apr. 3, 2006.

(51) Int. Cl.
*B01L 3/02* (2006.01)
*B01L 9/00* (2006.01)
*G01N 35/10* (2006.01)

(52) U.S. Cl.
CPC ............. *B01L 3/0237* (2013.01); *B01L 3/0231* (2013.01); *B01L 3/021* (2013.01); *B01L 9/50* (2013.01); *B01L 2300/023* (2013.01); *G01N 35/1009* (2013.01); *G01N 35/1011* (2013.01)
USPC ............ 73/863.01; 73/863; 417/278; 436/55; 436/180

(58) Field of Classification Search
CPC ....... B01L 3/0231; B01L 3/0237; B01L 9/50; B01L 2300/023; G01N 35/1009; G01N 35/1011; G01N 2035/1009; G01N 2035/1011
USPC .................. 73/863–863.01, 864.14; 137/552, 137/553–554; 222/1, 41, 52, 61; 250/574, 250/576; 417/63, 278; 436/55, 180
See application file for complete search history.

(56) References Cited

U.S. PATENT DOCUMENTS 3,864,571 A 2/1975 Stillman et al.
4,487,081 A * 12/1984 De Vaughn et al. ....... B01L 3/02
(Continued)

FOREIGN PATENT DOCUMENTS

EP 953843 A2 * 11/1999 ............. G01N 35/10
EP 1475177 A1 * 11/2004 ............... B23K 1/00
(Continued)

OTHER PUBLICATIONS

International Search Report and Written Opinion for corresponding PCT application No. PCT/US2007/008090, Feb. 26, 2008, 10 pp.

*Primary Examiner* — Thomas P. Noland
(74) *Attorney, Agent, or Firm* — Caseiro Burke LLC; Chris A. Caseiro

(57) ABSTRACT

A liquid aspirating and dispensing apparatus and method of using the apparatus. Among other elements, the apparatus includes a liquid handling device having one or more channel members, each of which has a removable liquid holding tip attached, and a signal transmitting device. A signal transmitted from the signal transmitting device may be used in a variety of ways to yield information regarding the performance of the apparatus. This information may be provided via direct detection of the signal by an operator of the apparatus. Alternatively, the signal may be detected by a programmable signal detecting device, interpreted by the apparatus, and then displayed in a form that is understandable to the operator. Furthermore, the liquid holding tip may be modified to enable different forms of signal transmission.

17 Claims, 13 Drawing Sheets

(56) References Cited

U.S. PATENT DOCUMENTS

| | | | |
|---|---|---|---|
| 4,790,183 A * | 12/1988 | Pfost et al. | G01N 35/1011 |
| 4,917,462 A * | 4/1990 | Lewis et al. | 359/368 |
| 4,944,922 A | 7/1990 | Hayashi | |
| 5,052,338 A * | 10/1991 | Maiorca et al. | 118/668 |
| 5,582,798 A * | 12/1996 | Meltzer | G01N 35/1011 |
| 5,960,530 A * | 10/1999 | Kerr et al. | 29/525 |
| 6,599,479 B1 | 7/2003 | Kietzmann et al. | |
| 6,905,657 B2 | 6/2005 | Hubbard et al. | |
| 6,916,000 B2 | 7/2005 | Weiss | |
| 7,416,706 B2 * | 8/2008 | Brunner et al. | B01L 3/02 |
| 7,481,978 B2 * | 1/2009 | Li et al. | B01L 3/02 |
| 7,618,589 B2 * | 11/2009 | Toi et al. | G01N 35/1011 |
| 8,100,007 B2 * | 1/2012 | Elsenhans et al. | G01N 35/1011 |
| 2003/0057347 A1 * | 3/2003 | Weiss | 248/558 |
| 2004/0048393 A1 * | 3/2004 | Colin et al. | 436/180 |
| 2007/0287192 A1 * | 12/2007 | Usowicz et al. | 436/161 |

FOREIGN PATENT DOCUMENTS

| | | | | |
|---|---|---|---|---|
| JP | 11033458 A | * | 2/1999 | B05C 5/00 |
| JP | 2005233649 A | * | 9/2005 | G01N 1/14 |
| JP | 2006053124 A | * | 2/2006 | G01N 1/14 |
| WO | WO 9325914 A1 | * | 12/1993 | G01N 35/06 |
| WO | WO 9715809 A1 | * | 5/1997 | G01F 23/26 |

* cited by examiner

APPARATUS AND METHOD FOR ASPIRATING AND DISPENSING LIQUID

CROSS REFERENCE TO RELATED APPLICATION

The present application is a divisional application, and claims the priority benefit, of U.S. nonprovisional patent application Ser. No. 11/684,182 filed Mar. 9, 2007 now U.S. Pat.No. 7,870,797, entitled "APPARATUS AND METHOD FOR ASPIRATING AND DISPENSING LIQUID" of the present assignees, which claims the priority benefit of U.S. provisional patent application Ser. No. 60/788,849, filed Apr. 3, 2006, entitled "APPARATUS AND METHOD FOR ASPIRATING AND DISPENSING LIQUID" of the same named inventors. The entire contents of the prior applications are incorporated herein by reference.

BACKGROUND OF THE INVENTION

1. Field of the Invention

The present invention relates to an apparatus and method to aspirate and dispense precise volumes of liquid, and more specifically to an apparatus and method to report a variety of types of information regarding apparatus performance or usage. The apparatus includes a signal transmitting device and an optional signal detecting device.

2. Description of the Prior Art

Many analysis methods used in biological, biotechnological, pharmaceutical, chemical and other types of research laboratories require accurate measurement and dispensing of small volumes of liquids that can range from one nanoliter to several milliliters. In one application, small volumes of liquid may be aspirated or dispensed from liquid handling devices having a single delivery channel or multiple channels configured to deliver or aspirate liquid simultaneously or sequentially. Specific examples include handheld single- or multichannel pipettes, configured to deliver or aspirate liquid samples from 1, 8 or 12 channels at a time, and automated delivery equipment configured to deliver or aspirate 96 or 384 liquid samples at one time.

In general, liquid handling devices, which also may be called pipettes, are syringes, each including a cylinder extended by a shaft or channel, and a liquid holding tip and a piston to slide within the cylinder. The piston may be activated manually or automatically by a motor over a selectable travel distance. The travel distance may be regulated manually or automatically using a computer. The use of liquid handling devices to aspirate and dispense precise volumes of liquids is well known. Also well known is the use of replaceable disposable tips to permit the sequential use of such devices in the handling of different liquids without contamination.

Replaceable tips are commonly formed from plastic and are a hollow, conical frustum with two open ends, one for mating with the shaft of the liquid handling device, and the other to permit liquid flow into and out of the interior of the tip.

For liquid handling devices, the level of aspiration and/or delivery must be both accurate and precise. At any given time the handling device may not be functioning within the requirements of the process or the specifications of the manufacturer. Many factors contribute to inaccuracy and imprecision of the liquid delivery and aspiration. For this reason it is necessary to repeat exactly procedures from one delivery and/or aspiration to the next to ensure correct operation and the integrity of the analysis. Therefore, the manufacturer must assure that the device functions correctly at the time of the analysis.

When using an air-displacement pipette specifically to aspirate liquid for quantitative delivery, it is important that the operator insert the tip to the correct depth in the liquid from which the aliquot is to be taken. An analysis of the importance of holding the tip at a proper depth within a liquid sample prior to aspiration is provided in International Organization for Standardization (ISO) standard, ISO 8655-2, dated 10 Oct. 2002. Additionally, under ISO standard 8655-6, dated 10 Oct. 2002, a typical tip insertion depth for aspiration should be 2-3 mm. Both ISO 8655-2 and ISO 8655-6 are incorporated herein by reference. Depending on the ambient light, on the angle of observation, on the optical density of the liquid being aspirated, and on the skill and visual acuity of the operator, this degree of accuracy can be difficult or impossible to achieve. If the insertion depth is incorrect, then the amount of liquid aspirated by the pipette will be incorrect. According to ISO 8655-2, the error in aspirated volume due to improper insertion depth can be up to 1%, well outside of the manufacturer's specified tolerance of many pipettes, typically less than 0.5%. It therefore would be desirable to develop a pipette and associated disposable tip that provide a visual aid to permit an operator to clearly see when the tip is inserted to the correct depth in the source liquid.

The same concerns apply to liquid aspiration by an automated (robotic) liquid handling device. With automated liquid handling devices, the function of sensing the correct insertion depth optimally is performed by a feedback sensor. The feedback sensor provides a signal to a control mechanism, which then directs the automated device to lower the tip until it is immersed to the correct depth. Where liquid aliquots are taken repeatedly from the same source vessel, the tip also must be repeatedly inserted more deeply into the vessel after each aspiration and before the next to maintain the correct insertion depth. An insertion-depth detection mechanism will accomplish this automatically to allow more accurate and reproducible liquid delivery by the automated liquid handler.

Another specific concern regarding the performance of liquid handling devices is the correct dispensing of liquid from the tip into the receiving vessel. If the tip is situated above the surface of liquid in the receiving vessel when liquid is dispensed (free-air or dry dispense), then surface tension of the liquid in the tip will often prevent all of the liquid from being discharged out of the tip. If the tip is held too deeply into the liquid in the receiving vessel (wet-dispense), then liquid may adhere to the outside of the tip and be inadvertently carried out when the tip is withdrawn. Finally, if an extra measure of air is dispensed to "blow out" any residue of liquid from within the tip, that air can form a bubble inside the liquid in the receiving vessel. Such bubbles generally aggregate on the side or bottom of the receiving vessel. Such a bubble is likely to lead to error when making an optical absorbance or emission reading. This latter effect especially is a problem when liquid is being dispensed into a microtiter plate because of the sample size and relative proportionate size of the bubble. Prior to dispensing an aliquot therefore, an automated liquid handler preferably should lower the tip until it touches, or is just below the surface of, the liquid in the receiving vessel.

What is needed therefore is a liquid handling device including one or more apparatus capable of detecting one or more of a multiplicity of parameters. These parameters include: (1) whether a tip is properly attached to a particular channel of the liquid handler; (2) that the proper type of tip is connected to the liquid handler; (3) the point at which the tip contacts the liquid surface, both when it is empty, for aspiration purposes, and when it is full, for dispensing purposes; (4) the point at which the tip's immersion depth in a liquid is proper, within an acceptable range for the particular pipette and tip design; (5) that liquid is present in the tip, after it has been withdrawn from the source vessel, to verify that aspiration has successfully taken place; and (6) that residual liquid is not present in the tip after dispensation is complete and after the tip is withdrawn from the receiving vessel, to verify that dispensation has successfully taken place.

SUMMARY OF THE INVENTION

The present invention is an apparatus and method that may be used to optimally aspirate and dispense precise volumes of liquid. More specifically, the invention is an apparatus which may be used in whole or in part to carry out a method for ensuring that the apparatus is optimally arranged to aspirate and/or dispense precise volumes of liquid.

The apparatus of the present invention includes a liquid handling device having a channel member. A liquid holding tip is connected to the channel member. Optimal aspiration of a liquid aliquot into the liquid holding tip and optimal dispensing of the liquid aliquot from the liquid holding tip requires that the liquid holding tip be of the proper type, and also requires that the liquid holding tip be properly arranged with respect to both its connection to the channel member and its position relative to a target such as a liquid sample from which the aliquot is to be aspirated or the vessel into which the aliquot is to be dispensed.

The apparatus of the present invention further includes a light transmitting device, and optionally, a light detecting device. These devices specifically may be used to ensure that the liquid holding tip is properly arranged for aspirating and/or dispensing.

The method of the present invention initially involves transmitting a light signal from the light transmitting device. The light signal then travels in any one of a variety of pathways. Specifically, in these pathways, the light travels within one or more media: air, a wall of the liquid holding tip, and optical fibers that are associated with the wall of the liquid holding tip. The light's travel in the pathway ends with the light being detected by the light detecting device or by the human operator of the apparatus. The detected light signal provides the apparatus or the operator with specific information regarding the liquid holding tip, such as whether it is of the proper type, whether it is properly connected to the channel member, or whether it is properly positioned with respect to a target. Based on this information, the operator may manually arrange the apparatus, or the apparatus may automatically arrange itself, to optimally aspirate and/or dispense the aliquot.

In an alternative embodiment of the apparatus, the liquid holding tip is modified to include one or more mechanisms for changing the travel of light within the tip. These light travel changing mechanisms provide information regarding tip selection, connection and/or positioning that is in an alternative form available when such mechanisms are omitted from the apparatus.

In general, the present invention is an apparatus for aspirating liquid from a target sample reservoir and dispensing the liquid to a target vessel. The apparatus includes a liquid handling device with a channel member, a liquid holding tip removably connectable to the channel member, and a signal transmitting device removably connectable or integral to either or both of the channel member and the tip, wherein the signal transmitting device is capable of transmitting an observable signal to the target as an indication of the position of the tip with respect to the target. Additionally, the present invention is a method for aspirating and dispensing liquids through a liquid holding tip from or to a target, the liquid holding tip forming a replaceable part of a liquid handling device. The method includes the steps of positioning the tip above or in the target, transmitting an observable signal from a signal transmitting device to the target, wherein the observable signal includes one or more indicia of position of the tip with respect to the target, detecting the signal, and determining from the detected signal one or more of: (1) whether the tip is properly attached to the liquid handling device; (2) that the proper type of tip is connected to the liquid handling device; (3) the point at which the tip contacts the surface of the liquid sample, both when the tip is empty for aspiration and when the tip contains a liquid aliquot for dispensation; (4) the point at which the position of the tip with respect to the target is acceptable; (5) that the liquid aliquot is present in the tip; and (6) that the aliquot or residual liquid is not present in the tip.

The details of one or more examples related to the invention are set forth in the accompanying drawings and the description below. Other features, objects, and advantages of the invention will be apparent from the description and the drawings.

DETAILED DESCRIPTION OF THE PREFERRED EMBODIMENTS OF THE INVENTION

Figure 1:
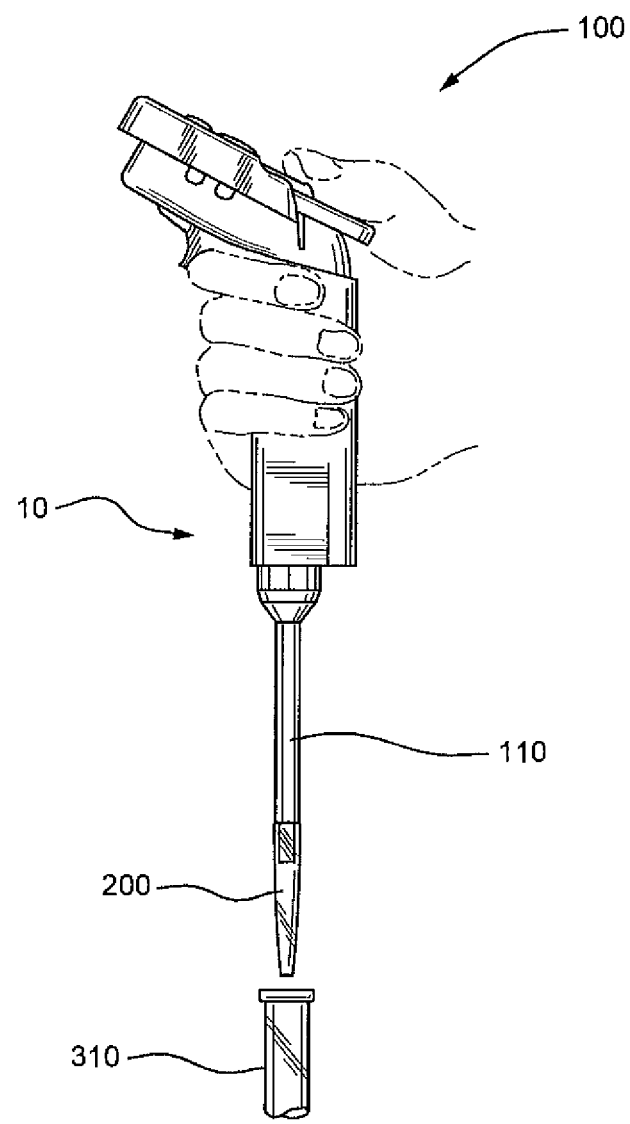
FIG. 1 is a side view of an embodiment of the apparatus of the present invention.

The present invention is an apparatus and method for aspirating and dispensing precise volumes of liquid. As shown in FIG. 1, the apparatus 10 includes among other components a liquid handling device 100 having a channel member 110 and a liquid holding tip 200, or simply, a tip 200.

The liquid handling device 100 of the apparatus 10 may be any of the liquid handling devices used by those ordinarily skilled in the art. It therefore is to be understood that the liquid handling device 100 may include one channel member 110 or may have a plurality of channel members 110, and that regardless of the number of channel members 110 that are included, each channel member 110 has its own tip 200. Further, the liquid handling device 100 may be operated manually or automatically.

It also is to be understood that the tip 200 preferably is removably connected to the channel member 110, but it may be integral with, and therefore undetachable from, the channel member 110.

Figure 2:
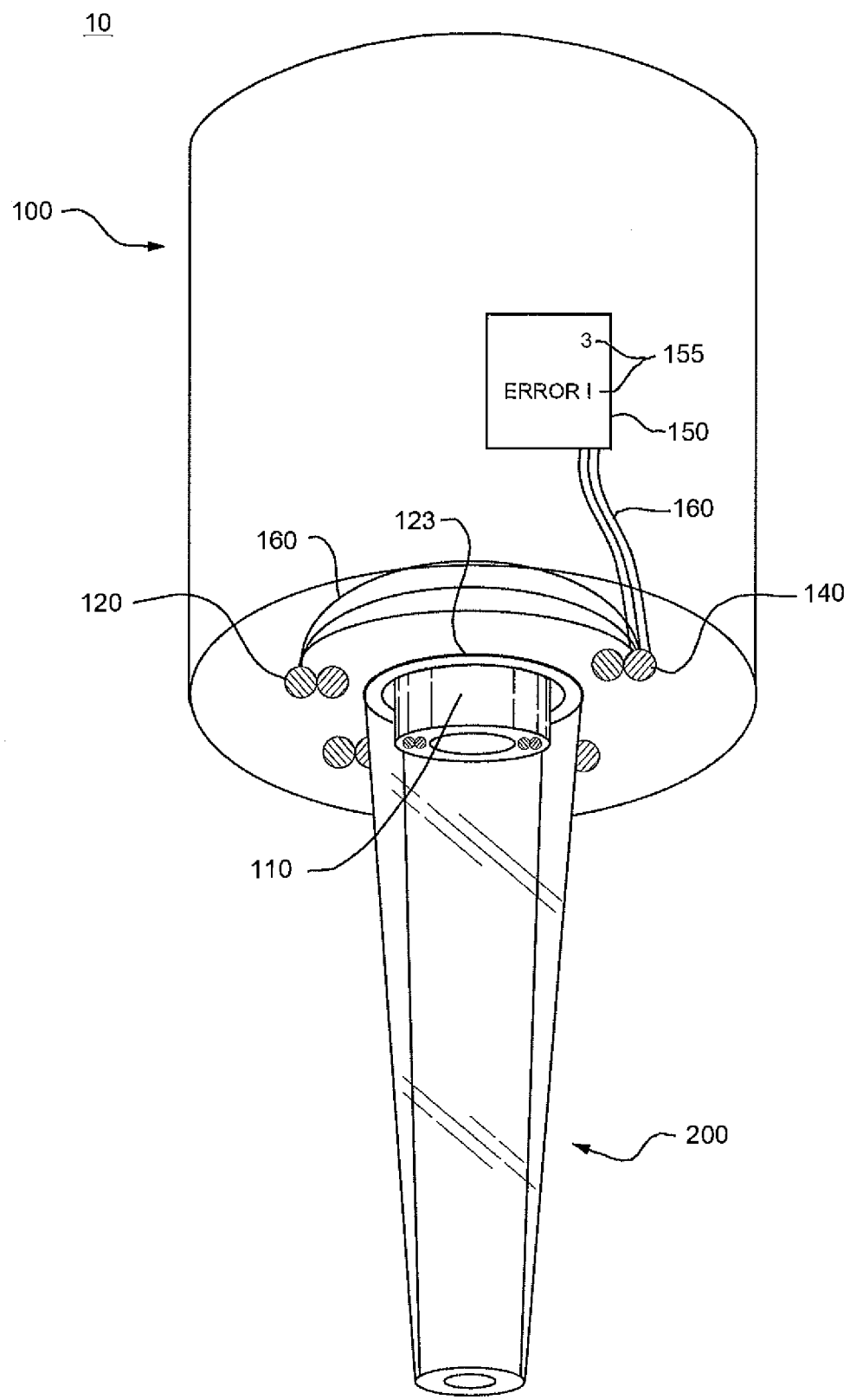
FIG. 2 is a longitudinal partial cross-sectional view of a simplified representation of a first embodiment of the apparatus of FIG. 1, showing an abbreviated form of the channel member and a simple view of the display panel.

Also as shown in FIG. 2, the apparatus 10 further includes a signal transmitting device 120, and optionally includes a signal detecting device 140. The apparatus 10 preferably includes a light transmitting device as the signal transmitting device 120, and a light detecting device as the signal detecting device 140. Hereinafter, therefore, the signal transmitting device 120 specifically will be referred to as being the light transmitting device 120, and the signal detecting device 140 specifically will be referred to as being the light detecting device 140. The apparatus 10 includes logic circuitry 160 connectable to the light transmitting device 120, the light detecting device 140, if any, and a display device 150, if any. The display device 150 may be used to display information associated with the use and/or operation of the apparatus 10.

It is to be understood that the light transmitting device 120 and/or the light detecting device 140 may be connected to or integral to the liquid handling device 100 or either or both may not be connected to the liquid handling device 100. It is also to be understood that the apparatus 10 may include more than one light transmitting device 120 and/or one or more light detecting devices 140, as shown in subsequent drawings. Exemplary devices that may be used as the light transmitting device 120 include light emitting diodes (LEDs) or solid state diode lasers. LEDs and diode lasers are both commonly manufactured components available from a number of sources including, for example, Hamamatsu Photonics of Hamamatsu City, Japan, or Bridgewater, N.J. When the signal is intended to be viewed by the user, an LED or diode laser with a center wavelength in the visible region of the electromagnetic spectrum (~400-700 nm) will be chosen. If no human viewing is required and signal processing is performed by the logic circuitry 160, a wavelength in the visible region or the near-infrared region (NIR, beyond ~700 nm) can be selected. Either is suitable for the purpose of the present invention. Exemplary devices that may be used as the light detecting device 140 include light detecting silicon photodiodes. Silicon photodiodes are also available from a variety of sources including but not limited to the Hamamatsu source identified herein.

The apparatus 10 is configured in one or more of several ways to enable an operator to aspirate and/or dispense precise volumes of liquid by generating information regarding its own performance. Either the human operator of the apparatus 10, or where the apparatus 10 is automated, the apparatus 10 itself, may then use this information as a basis to adjust the apparatus 10 to perform optimally.

Information regarding apparatus 10 performance may be, but is not limited to being, one or more of the following: (1) that the tip 200 is properly attached to the channel member 110; (2) that the proper type of tip 200 is connected to the channel member 110; (3) the point at which the tip 200 contacts the surface of a liquid sample, both when the tip 200 is empty, for aspiration purposes, and when the tip 200 is holding a liquid aliquot, for dispensing purposes; (4) the point at which the immersion depth of the tip 200 in a liquid sample is proper, that is, when the tip 200 is immersed within the liquid to an extent which is within an acceptable range for the particular liquid handling device 100 and tip 200 used; (5) that a liquid aliquot is present in the tip 200, such as after the liquid aliquot has been withdrawn from a liquid sample to verify that aspiration has successfully been completed; and/or (6) that residual liquid is not present in the tip 200, such as after dispensation is complete and after the tip 200 is withdrawn from a liquid sample to verify that dispensing has been completed successfully.

To provide these and other types of information, the apparatus 10 is capable of being used according to one or more of a plurality of methods, which, in the aggregate, require that the apparatus 10 be configured in one or more of a plurality of ways. The exact nature of the information provided specifically depends upon the method, and therefore, the configuration, used. A primary method of using and configuring the apparatus 10 of the present invention and several variations in one or more of the primary steps associated with the method are described herein.

In all methods of using the apparatus 10, there is at least one positioning step, at least one light transmission step, at least one light detection step and at least one information reporting step. Further, in some, but not in all, methods of using the apparatus 10, the at least one light detection step and the at least one reporting step may be performed substantially simultaneously.

In the light transmission step, light is transmitted from the light transmitting device 120 and travels within one or more of three media: air, an optical light fiber, and the tip 200 itself. Further, during the transmission step, the light follows a specific pathway before being detected in the detection step, either by the human operator of the apparatus 10 or by the light detecting device 140.

Figure 3:
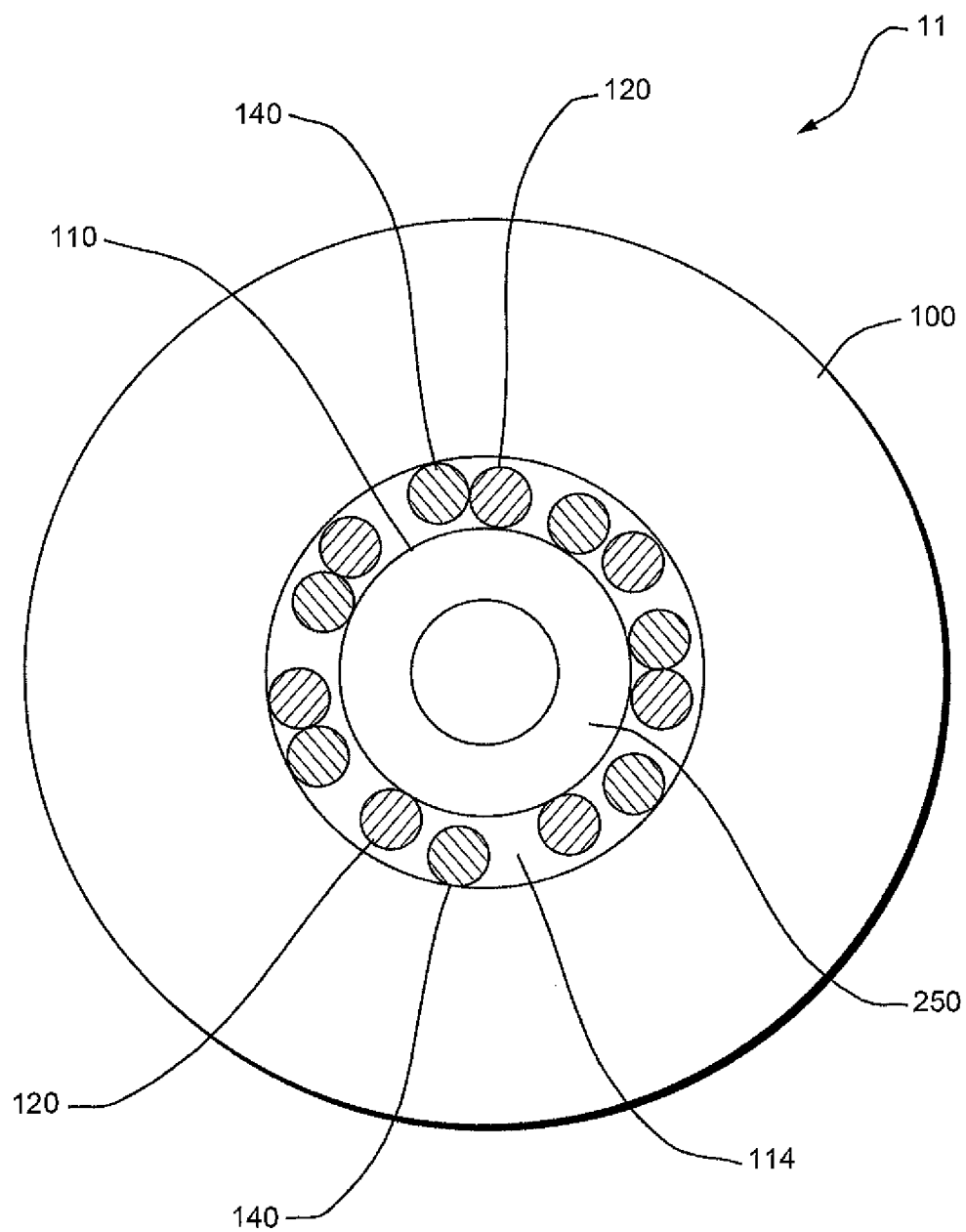
FIG. 3 is a transverse cross-sectional view of the channel-tip interface of the embodiment of the apparatus of FIG. 2, showing a plurality of point sources and point detectors.

A first embodiment of the present invention is shown in transverse cross-sectional view at an interface of the channel member 110 and the tip 200 as apparatus 11 in FIG. 3. The apparatus 11 includes the liquid handling device 100 having the channel member 110 and location 250 where the tip 200 (not shown in this figure) engages the channel member 110. The apparatus 11 further includes a plurality of light transmitting devices 120 and a plurality of light detecting devices 140, integrally or removably affixed to an apparatus interior at or near channel-tip interface 112. Specifically, the light transmitting devices 120 are affixed to an interior wall 114 of the channel member 110 at the interface 112. The light detecting devices 140 are similarly affixed to the channel member 110. The light transmitting devices 120 are arranged within the apparatus interior to transmit light within air external to the tip 200. In a first alternative arrangement, the light transmitting device 120 is affixed to the liquid handling device 100 within the channel member 110 above the interface 112. In a second alternative arrangement, the light transmitting device 120 is affixed within the tip 200 below the interface 112. In a third alternative arrangement, the light transmitting device 120 is affixed to a wall 240 (not shown in this figure) of the tip 200.

Figure 4:
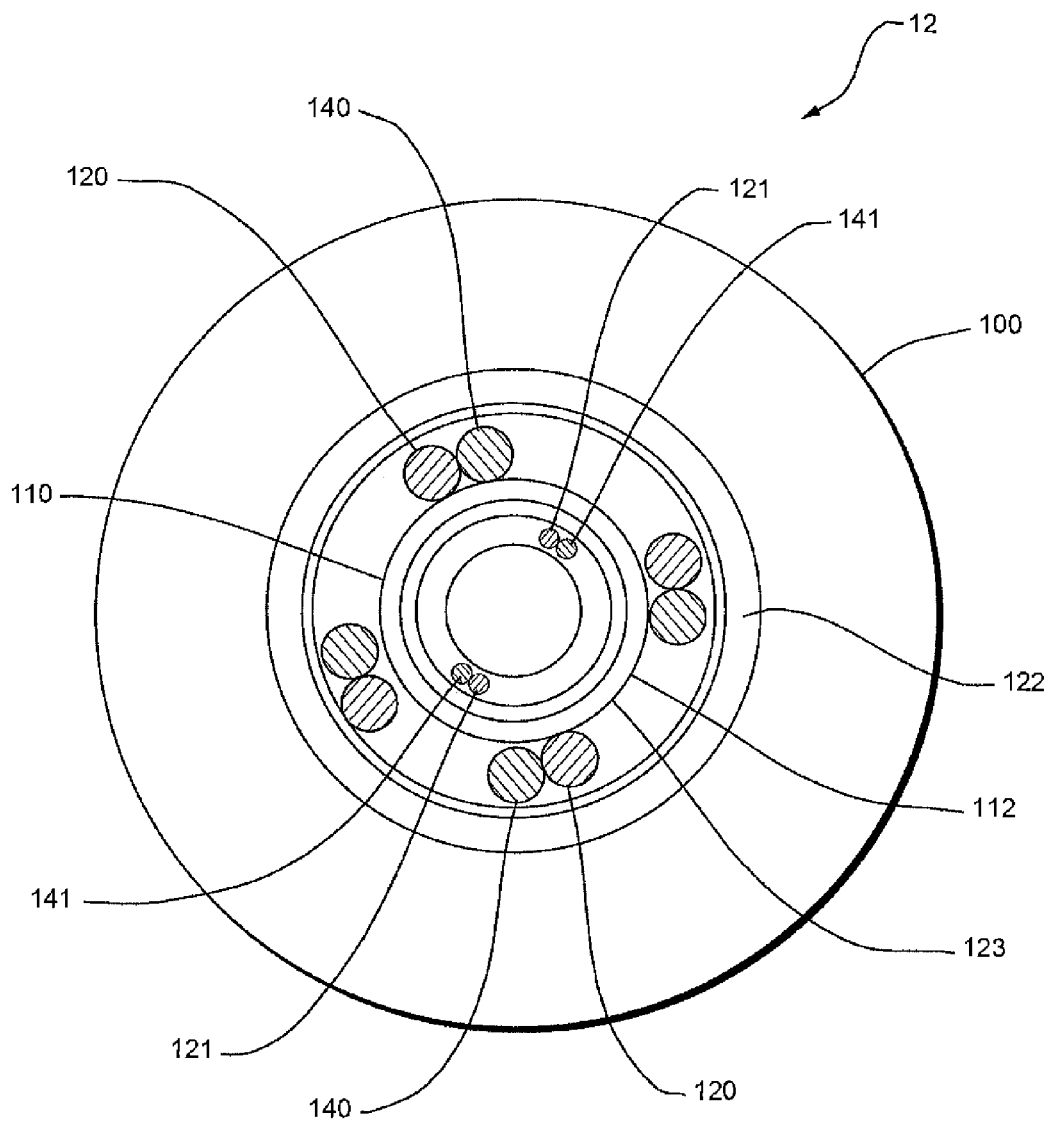
FIG. 4 is a transverse cross-sectional view of the channel-tip interface of a second embodiment of the apparatus of the present invention, showing a plurality of point sources and point detectors and two annular sources.
Figure 5:
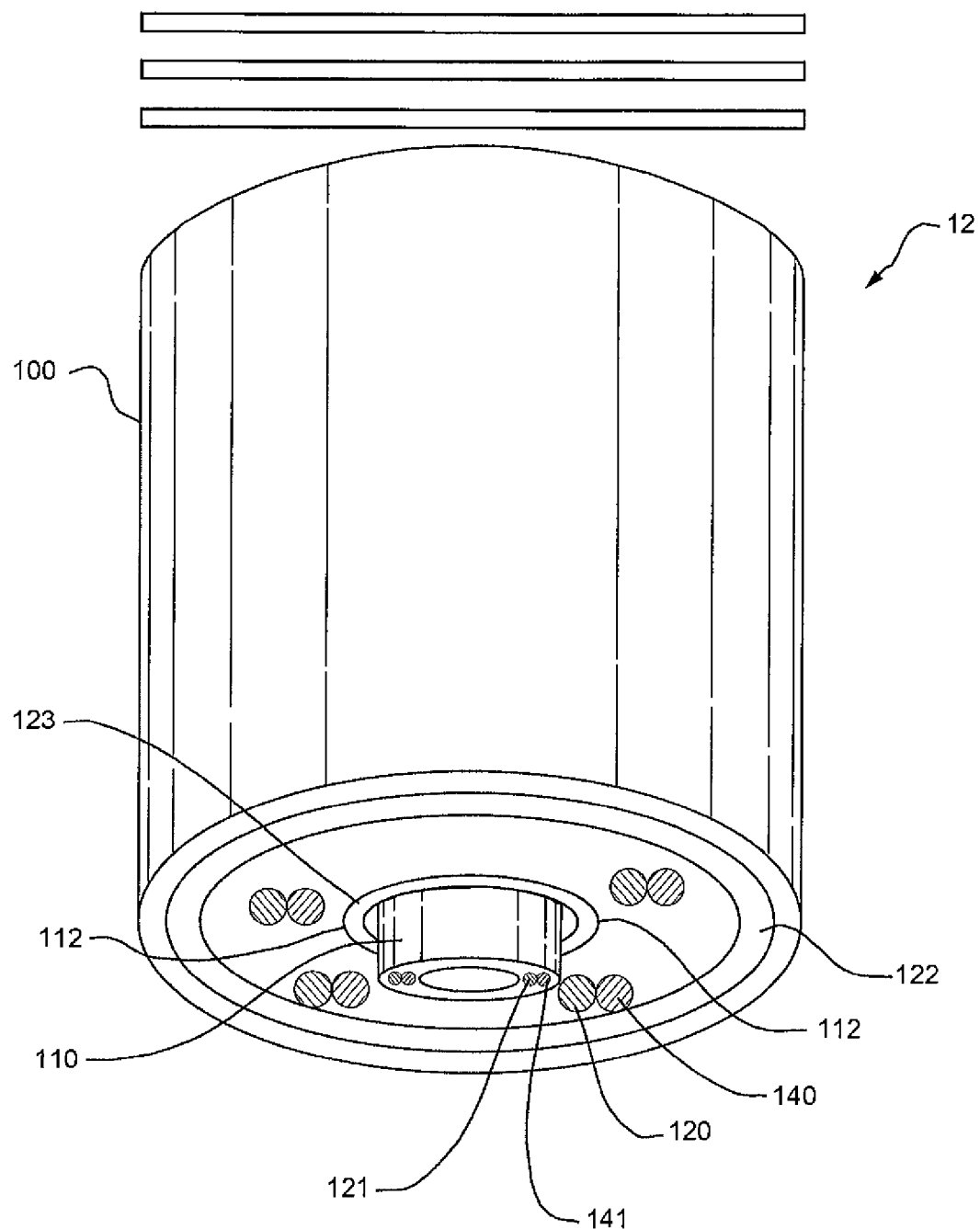
FIG. 5 is a perspective view from below of the second embodiment of the apparatus shown in FIG. 4 without the tip attached.

A second embodiment of the present invention is shown as apparatus 12 in FIGS. 4 and 5. The apparatus 12 includes the liquid handling device 100 having the channel member 110 and location 250 where the tip 200 (not shown in these figures) engages the channel member 110. The apparatus 12 further includes a plurality of external light transmitting devices 120 affixed to the channel member 110 at channel-tip interface 112 external to where the tip 200 is joined to the channel member 110. The apparatus 12 also includes a plurality of external light detecting devices 140 affixed to the channel member 110 at the channel-tip interface 112 external to where the tip is joined to the channel member 110. The light transmitting devices 120 transmit light within air external to the tip 200 and light detecting devices 140 detect light observable in air external to the tip 200.

With continuing reference to FIGS. 4 and 5, the apparatus 12 includes a plurality of internal light transmitting devices 121 affixed to the channel member 110 at channel-tip interface 112 internal to where the tip 200 is joined to the channel member 110. The apparatus 12 also includes a plurality of internal light detecting devices 141 affixed to the channel member 110 at the channel-tip interface 112 internal to where the tip 200 is joined to the channel member 110. The light transmitting devices 120 transmit light within air internal to the tip 200 and light detecting devices 140 detect light observable in air internal to the tip 200. The light transmitting devices 121 and the light detecting devices 141 may be used to determine whether an aliquot of liquid or residual liquid is located within the tip 200.

Figure 6:
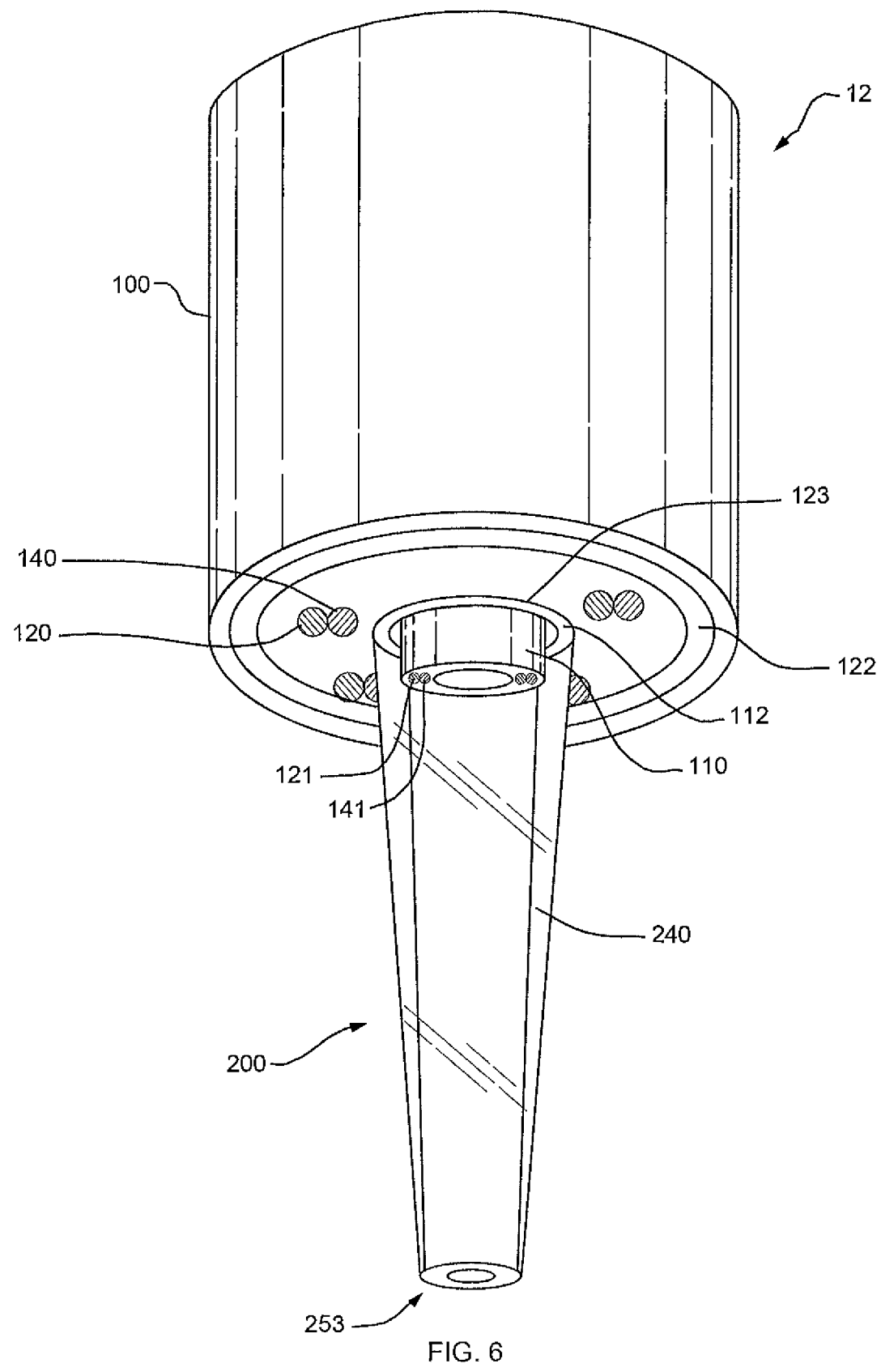
FIG. 6 is a perspective view from below of the second embodiment of the apparatus shown in FIG. 4 with the tip attached.

Further, the apparatus 12, includes external light transmitting device 122. The light transmitting device 122 transmits light in a selectable shape, such as an annulus based on the annular shape of light transmitting device 122 shown in the figure, within air external to the tip 200. The apparatus 12 also includes integral light transmitting device 123, which is arranged to transmit light within wall 240 of the tip 200. FIG. 6 shows the light transmitting devices, including the integral light transmitting device 123 as part of the apparatus 12 with the tip 200 attached. The integral light transmitting device 123 is specifically aligned to transmit light within wall 240 of the tip 200 to a target, such as a liquid sample 310 as shown in FIG. 1. In this arrangement, the wall 240 of the tip 200 serves as an optical waveguide, in which the light travels within the wall 240 until exiting through end 253. The angle of reflection internal to the body of the tip 200 must be greater than a critical angle given by Snell's Law according to the formula:

$$\sin\alpha_c = \frac{n_o}{n_i};$$

where $\alpha_c$ is the critical angle, $n_i$ is the index of refraction of the material of which the tip 200 is constructed, and $n_o$ is the index of refraction of the media (air or sample solution) adjacent to the tip wall 240.

Proper light propagation within the wall 240 of the tip 200 also requires the tip 200 to be constructed of a transparent waveguide-quality material. An exemplary material from which the tip 200 may be formed is polymethylpentene. Polymethylpentene is highly transparent and is exceptionally resistant both to chemicals and to wetting. Although polymethylpentene is a preferred material, it is to be understood that the tip 200 is not limited, however, to being formed from polymethylpentene.

Figure 7:
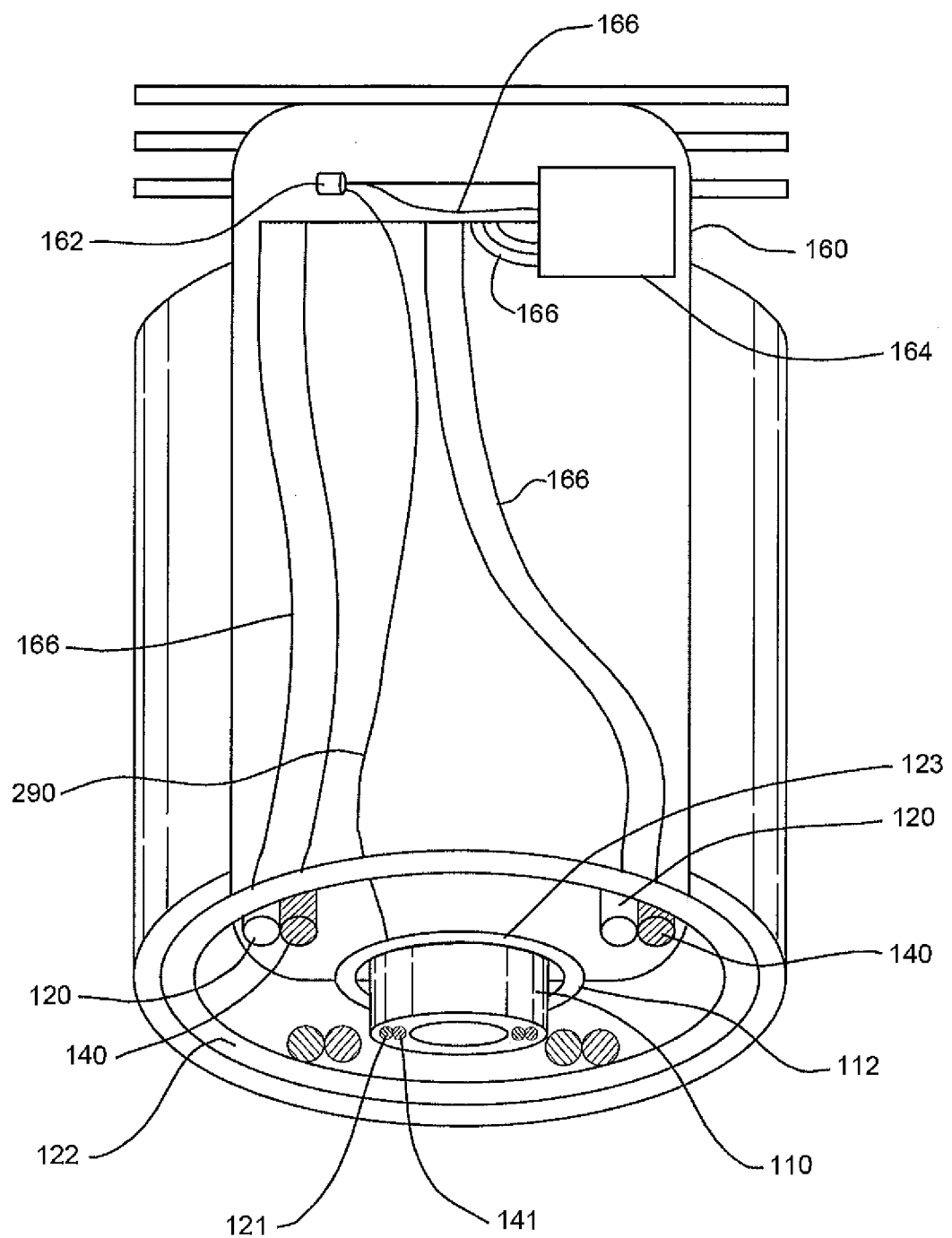
FIG. 7 is a perspective view from below of the second embodiment of the apparatus shown in FIG. 4 without the tip attached and showing a simplified representation within the liquid handling device of the electrical connections between the light source and detectors and the logic circuitry, wherein the LED light sources and the light detectors are positioned at the channel-tip interface.

As illustrated in FIG. 7, the light transmitting devices, such as light transmitting devices 120, and the light detecting devices, such as light detecting devices 140, may be positioned at or near the channel-tip interface 112. The light transmitting devices 120 are coupled to the logic circuitry 160 including a light generator 162 through transmitter 164 and leads 166. Additionally, light transmitting device 123 and/or light transmitting device 122 may be coupled directly to the light generator 162 through optical fiber 290.

Figure 8:
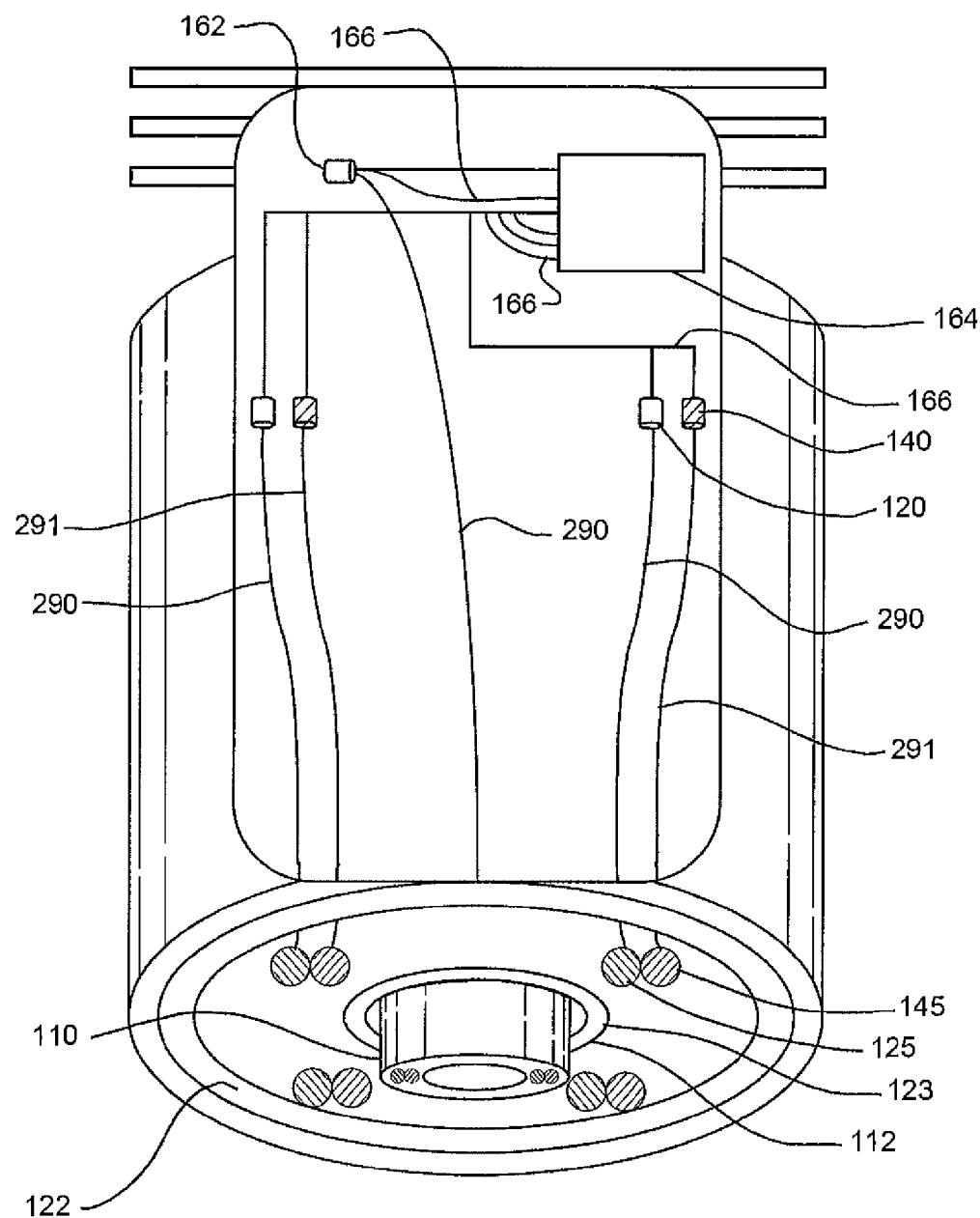
FIG. 8 is a perspective view from below of the second embodiment of the apparatus shown in FIG. 4 without the tip attached and showing a simplified representation within the liquid handling device of the electrical connections between the light source and detectors and the logic circuitry, wherein the LED light sources and the light detectors are positioned remote from the channel-tip interface within the channel member.

As illustrated in FIG. 8, the light transmitting devices, such as light transmitting devices 120, and the light detecting devices, such as light detecting devices 140, may be positioned away from the channel-tip interface 112. They are preferably spaced away from the tip 200 (not shown in this figure) so as to minimize heating of the liquid sample or air within the tip lumen. The light transmitting devices 120 are coupled to the logic circuitry 160 and the light generator 162 through leads 166. However, the channel-tip interface includes light transmitting ports 125 and light detecting ports 145 for transmitting and detecting light. The light is transmitted through optical fibers 290 and detected through optical fibers 291. Additionally, light transmitting device 123 and/or light transmitting device 122 may be coupled directly to the light generator 162 through optical fiber 290.

Figure 9:
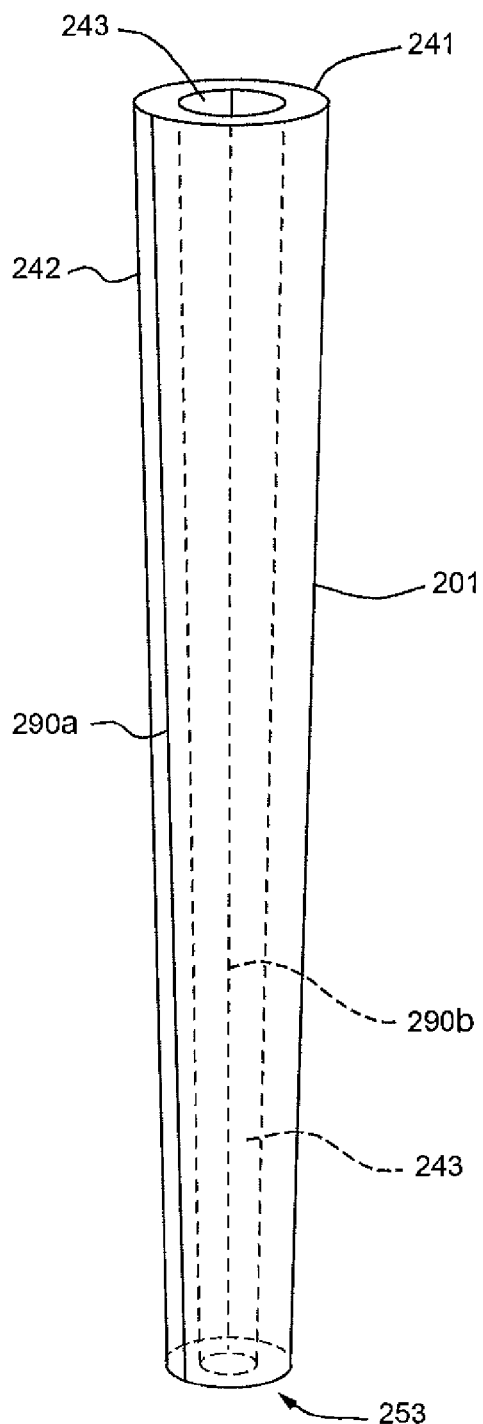
FIG. 9 is a longitudinal view of a tip of the present invention with a light-transmitting fiber within the lumen of the tip and a light-transmitting fiber on the exterior of the tip.
Figure 10:
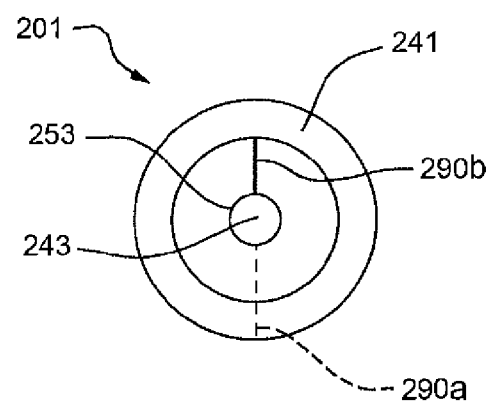
FIG. 10 is a top cross-sectional view of the tip of FIG. 9.

The tip 200 of the invention as described with respect to FIG. 6 and related figures may be any type of conventional tip known for use in liquid handling devices. An alternative tip arrangement may be used in the apparatus 10 of the present invention. Specifically, as illustrated in FIGS. 9 and 10, tip 201 includes one or more of the optical fibers 290 adjacent to tip wall 241. The optical fiber 290 is represented as two separate fibers in FIGS. 9 and 10, wherein fiber 290a extends along the exterior surface 242 of the tip 201 and fiber 290b extends along the wall within the lumen 243 of the tip 201. The optical fibers 290a/290b may be integrally affixed to tip wall 241, the optical fibers 290a/290b may form an integral part of the tip wall 241, and they may extend through to tip end 253. The optical fibers 290 may also alternatively be attached to the tip wall 241 rather than integrally affixed to or forming part thereof. The optical fibers 290a/290b function as light waveguides, thereby eliminating the need to fabricate the tip 201 of a light transmitting material. For example, the tip 201 may be fabricated of polypropylene. That is, when the present invention includes the use of one or more optical fibers 290a/290b, it is not necessary for the tip 201 to carry a light signal, thereby eliminating the need to fabricate all or a portion of the tip 201 of waveguide-quality material.

Figure 11:
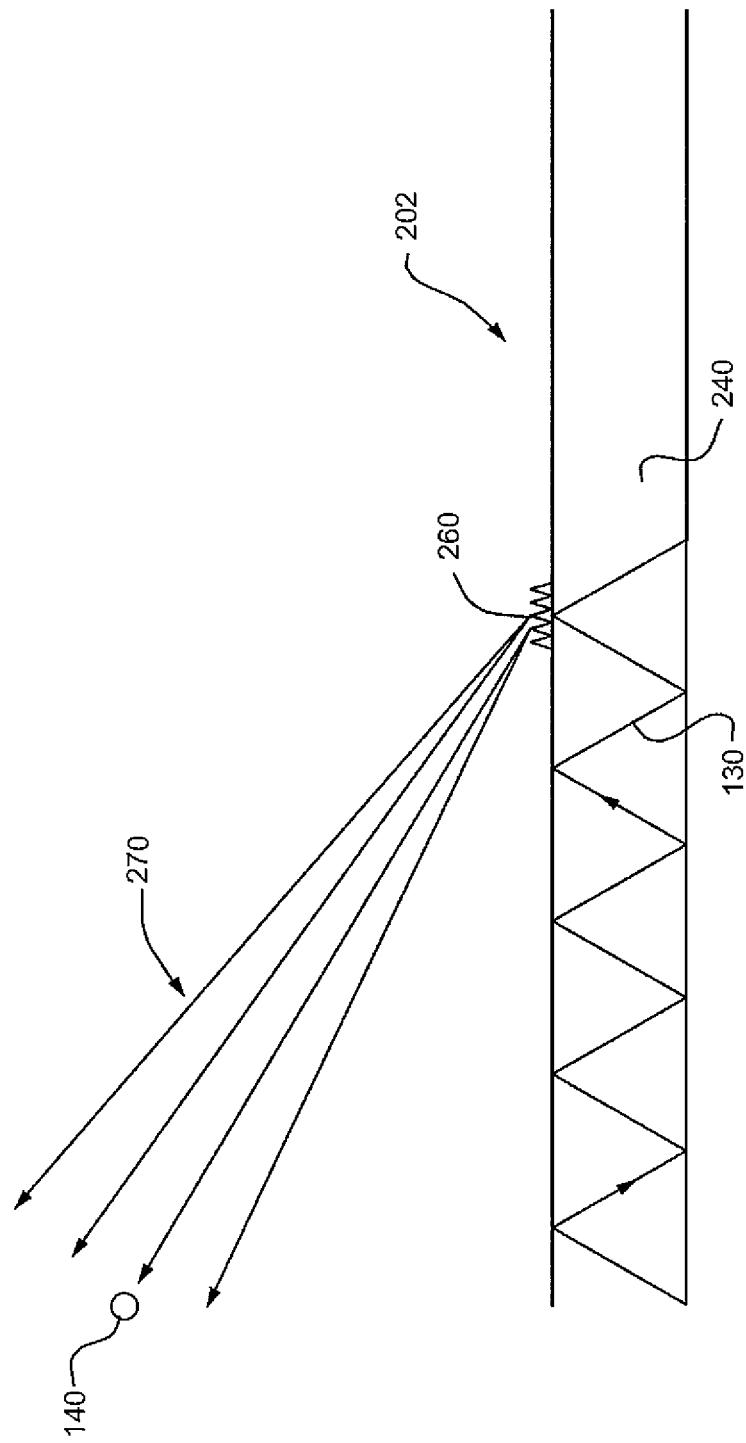
FIG. 11 is a close-up longitudinal cross-sectional view of a tip of the present invention including light transmission within the tip wall and an out-coupling device, showing light scatter from the out-coupling device and a detector positioned at the channel-tip interface.

A second alternative embodiment of the tip of the invention is a tip including any one or more of a plurality of out-coupling mechanisms. FIG. 11 shows one example of a portion of a tip 202 including an out-coupling mechanism 260. The tip 202 may be of the type capable of transmitting light through tip wall 240, in the form of a light waveguide to pass light 130 from an integral light transmitting device 123 within the tip wall 240. In the arrangement of the tip 202 shown, the out-coupling mechanism 260 includes one or more dispersion elements which are used to out-couple the light 130 propagating within the tip wall 240 and to establish the direction that the out-coupled light will travel upon exiting the tip wall 240. See, for example, out-coupled light pathways 270, which out-coupled light may be detected by light detecting device 140. Exemplary dispersion elements are diffraction gratings formed as parallel grooves that are substantially equally spaced in a defined period, the grating period further defining the direction in which light will exit the walls of the tip. Exemplary diffraction gratings include those created by holographic processes and replica grating formation processes, as well as others known to those with skill in the art of diffraction grating formation. Alternatively, the out-coupling mechanism 260 may be a scattering element such as scattering particles positioned in the tip wall 240, a roughened surface or area of the tip 202, or a refractive element, such as a change in the geometry of the wall of the tip 202. It should be understood that any arrangement for scattering the light may be employed and that the scattering element is not limited to the three examples listed. (It is also to be understood that the optical fibers 290/291 may include any one or more of the described out-coupling mechanisms. When the optical fibers 290/291 include one or more of these out-coupling mechanisms, the included out-coupling mechanisms function in the same manner as described above.)

Light 130 transmitted at the transmission step ultimately must be detected at the detection step. Detection of the light 130 may be made solely by the operator of the apparatus 10, solely by the light detecting device 140, or by both the operator and the light detecting device 140.

Light 130 detected solely by the operator may provide the operator with specific information regarding apparatus 10 performance, which the operator then may use as a basis to manually adjust the apparatus 10 so that it performs optimally. For example, based on direct observation of the light 130, the operator may determine that a tip is in some way defective, and accordingly, remove that tip and replace it with another tip. Whenever only the operator detects the light 130, the signal detection step and the information reporting step of the method previously described are essentially performed at the same time.

Whenever a light detecting device 140 is used to detect light 130, logic circuitry 160 connected to the light detecting device 140 processes raw data regarding the light 130 detected, such as the change in signal intensity that occurs when the end of the tip contacts the liquid, into specific information regarding apparatus 10 performance. For example, the logic circuitry 160 may use the raw data corresponding to a change in light intensity upon contact of the tip 200 with liquid as detected by the light detecting device 140 to determine that the tip 200 is at a particular position. More specifically, when the light reaches the end 253 of the tip 200, some of it may be redirected (commonly done with fiber optics) back towards the source end. The light detecting device 140 may be used to monitor the amount of light coming back to the source end. The relative amount of light coming back will change when the tip 200 contacts the target, which is the surface of a sample solution. The light detecting device 140 detects when the tip 200 has made contact with the sample. The logic circuitry 160 then provides the operator with information dictating how far the tip is to be inserted into the sample.

Information regarding performance of the apparatus 10 processed by the logic circuitry 160 may be used in a variety of ways. In one of these ways, the information may be reported by the apparatus 10 to its operator in a form understandable to the operator. Specifically, this reporting to the operator may be done by using the light transmitting device 120 and/or the display device 150.

Reporting of performance information by the apparatus 10 to the operator via the display device 150, for example, may be accomplished as shown in FIG. 2. In FIG. 2, the display device 150 is preferably a liquid crystal display (LCD) that is capable of displaying one or more icons 155. However, it is to be understood that the display device 150 is not limited to being an LCD. A light emitting diode (LED) display would not be useful for displaying icons, but different colored LEDs in an array would be useful for signaling binary conditions such as success or error conditions.

Where an LCD is used as the display device 150, the exact nature of the one or more icons 155 appearing on the LCD provides the operator with specific information regarding the apparatus 10. The one or more icons 155 therefore may indicate one or more performance indicia of apparatus status. For example, consider a case in which a liquid handling device 100 having twelve of the channel members 110 is being used, and the apparatus 10 determines that both the third and eleventh channel members are not ready for use. For example, they may have no tip, the wrong tip, an incorrectly connected tip, or an improperly positioned tip with respect to a target. The logic circuitry 160 might then direct the LCD to display the numbers "3" and "11" for the purpose of reporting their improper status to the operator. Furthermore, more specific information also may be included about channel members "3" and "11." For example, the "3" may appear and disappear intermittently, such as for reporting that there is no tip 200 connected to channel member "3." As another example, the "11" may appear crossed out, such as for reporting that the tip 200 connected to channel member "11" is of an improper type.

Referring to a prior example, whenever the tip 200 is too far removed from the target, the display device 150 might display a particular icon 155 that generally represents that it is not at the desired position. Further, the display device 150 might display an icon 155 that provides more specific information, such as that the tip 200 is a specific distance too far removed from the target.

Alternatively, information gleaned from the light 130 by the apparatus 10 may be used by the apparatus 10 as a basis for automatically adjusting the performance of the apparatus 10. For example, the apparatus 10 may determine, based on the information detected, that a tip 200 is not properly positioned with respect to a liquid sample for the purpose of aspirating or dispensing a liquid aliquot, and accordingly, move the tip 200 into proper position without the aid of the operator.

Further, the light transmitting device 120 alone may be used to report information interpreted by the logic circuitry 160 to the operator. Specifically, light may be transmitted in a variety of manners by the light transmitting device 120, with each manner representing a particular type of information. For example, the light may be transmitted by modulating intensity and/or wavelength. For example, a tip 200 determined by the apparatus 10 to have an unacceptable status may illuminate, whereas a tip 200 having a desired status may fail to illuminate, or vice versa. As another example, an improperly arranged tip 200 may repeatedly cycle through periods of illumination and non-illumination, while a properly arranged tip 200 may remain continuously illuminated or non-illuminated, or vice versa. As yet another example, an improperly arranged tip 200 may illuminate as one color, such as red, and a properly arranged tip 200 may illuminate as another color, such as green.

Figure 12:
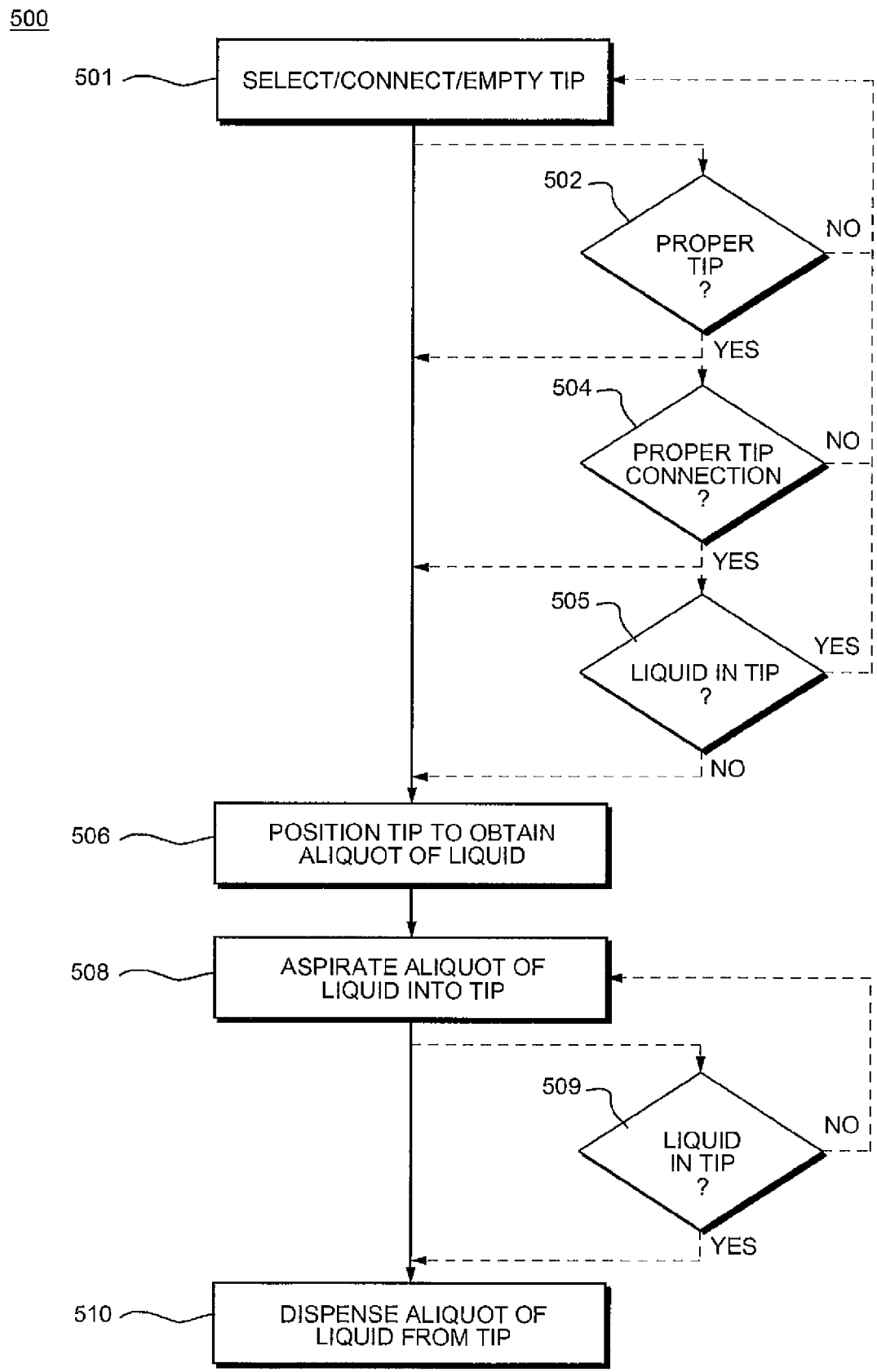
FIG. 12 is a simplified block representation of the primary steps of a method of aspirating and dispensing a liquid aliquot with the apparatus of the present invention.

The apparatus 10 of the present invention and one or more of the variants described herein may be used to perform a liquid aspiration and dispensation method 500 including a plurality of primary steps as represented in FIG. 12. The method 500 includes additional and optional steps to be described herein. Initially, and with reference to FIGS. 12 and 13, a first step 501 involves selecting a removably affixable tip 200 for attachment to a channel member 110 of a liquid handling device 100 as previously described. The channel member 110 includes one or more light transmitting devices 120 affixed thereto. The channel member 110 also includes one or more light detecting devices 140 affixed thereto. The tip 200 is affixed to the channel member 110 at interface 112, either by reversibly screwing it on, or by creating a friction fit or any of the other methods familiar to those skilled in the art.

The step of selecting a tip 501 includes the step of connecting the tip 200 to the channel member 110. The method 500 may include optional step 502 of determining whether the tip 200 selected is the type suitable for the intended purpose and optional step 504 of determining whether an affixed tip is properly connected to the channel 110. For this step, the tip of FIG. 11 may be used, wherein the integral light transmitting device 123 is arranged to enable light transmission within the tip wall 240, wherein the tip wall 240 includes the out-coupling mechanism 260. Light 130 is transmitted within the tip wall 240 by the integral light transmitting device 123 to exit the tip wall 240 through the out-coupling mechanism 260 where it is then detected by the light detecting device 140. For example, the light detecting device 140 may be positioned on the apparatus 10 such that it will detect selectable out-coupled light from the tip. A particular light detecting device may be configured and arranged to detect light of certain characteristics. That light of certain characteristic may correspond to an out-coupled portion of light transmitted through the tip wall 240, which out-coupling is the result of the positioning of an out-coupling mechanism grating. A second light detecting device may be positioned on the apparatus to detect out-coupled light produced through a second out-coupling mechanism grating physically spaced from the first grating. Alternatively, the second out-coupling mechanism may simply generate a different detectable light out-coupling from the tip. The detected light information from the light detecting devices may be used by the logic circuitry 160 to determine proper tip selection and attachment. The logic circuitry 160 may then direct the display device 150 to report that the proper tip is properly connected to the channel member 110 according to any one or more of the variety of ways described before. A plurality of out-coupling light mechanisms may also be employed to determine whether the tip has been immersed to a suitable depth within a sample.

It is to be noted that the present invention takes advantage of the concept of light back-reflection, which is the propagation of light back toward its origin. The invention is capable of detecting light signal changes that occur at the interface between two media having different refractive indices, which is either the interface between the tip 200 and air or between the tip 200 and liquid. Specifically, in regard to the present invention, light travels to the end 253 of the tip 200, the end 253 being defined as the interface between the medium of tip 200 and the opposing medium, which is either air or liquid. As the light intersects the end 253 of the tip 200, a portion of the light will be reflected by the interface, while the remaining portion will be refracted across the interface. The refracted portion of the light will cross the interface between the tip 200 medium and the opposing medium (either air or liquid), thereby escaping the tip 200 medium, and will continue to travel away from the tip 200 through the opposing medium (either air or liquid). The reflected portion of the light will be directed back toward its origin, and will propagate back through the tip 200, which effect is commonly referred to as "back-reflection". The relative proportion of the light that will be back-reflected at the end 253 of tip 200 is defined by the reflectivity coefficient R:

$$R_{1,2} = \left(\frac{\eta_1 - \eta_2}{\eta_1 + \eta_2}\right)^2;$$

where, in the context of the present invention, $R_{1,2}$ is the percentage of light reflected at the interface between the tip 200 medium and the opposing medium (either air or liquid), and $\eta_1$ and $\eta_2$ are the angular dependent refractive indices of the tip 200 medium and the opposing medium (either air or liquid), respectively. This equation demonstrates that the amount of light reflected at any interface between two different media, such as, for example, the tip medium 200 and the opposing medium, is dependent upon the refractive indices of those media. Because the tip 200 medium and the opposing medium have different refractive indices, a portion of the incident light is reflected back into the tip 200 at the interface between the end 253 and the opposing medium. This reflected light may be used, for example, to determine that the end 253 is touching the surface of the sample 310 or is immersed in the sample 310. This is true because the intensity of the light that is back-reflected into the tip 200 will change, as detectable by the light detecting device 140, whenever the end 253 leaves air and contacts the liquid sample 310 due to the difference in refractive indices between the air and the liquid sample 310. The optical fibers 290/291 may be substituted for the tip 200 to achieve this same result as they may be used in the process of detecting light signal changes.

Figure 14:
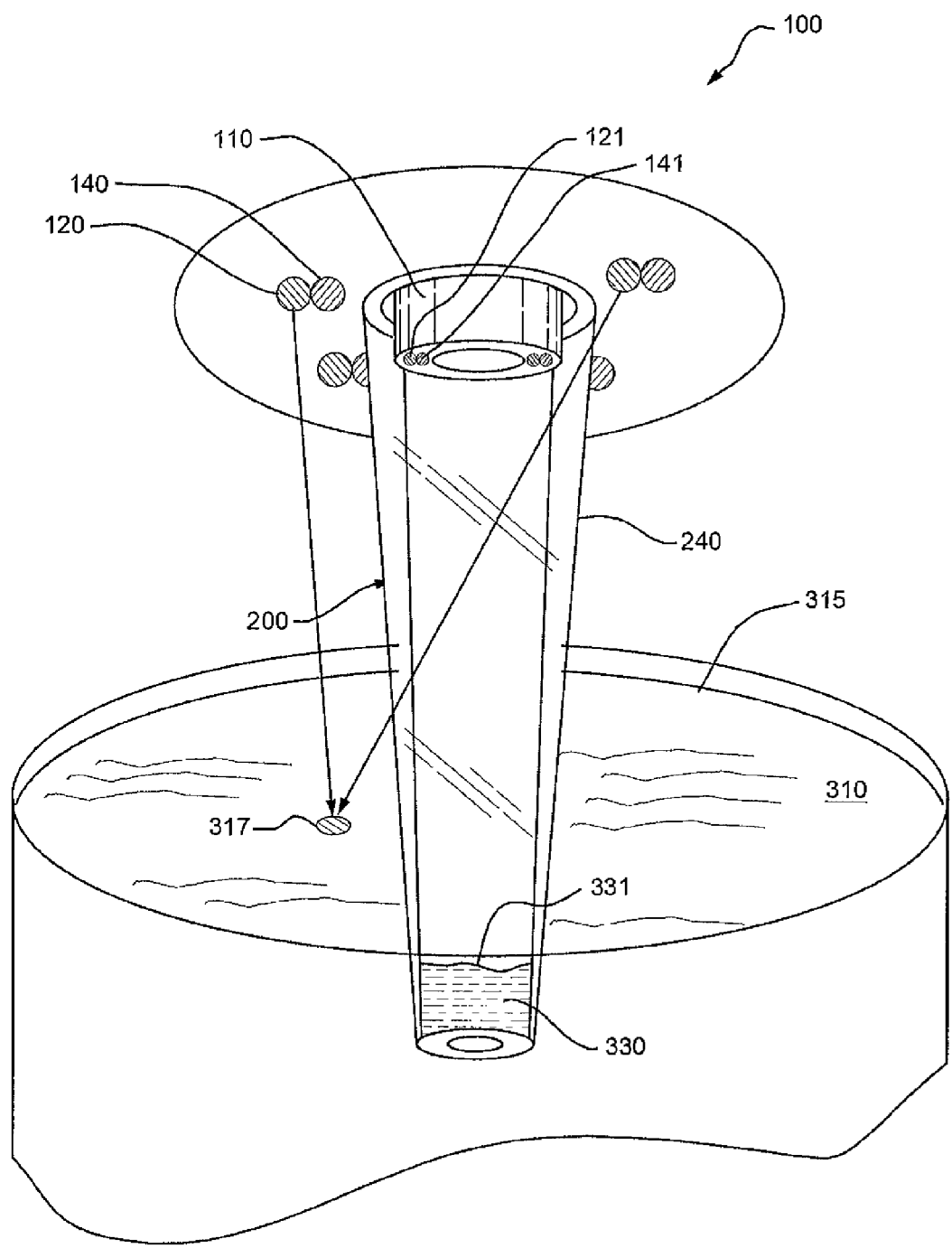
FIG. 14 is a side view of a second embodiment of the apparatus as it is positioned within a source of a liquid being aspirated.

Upon confirming that the proper tip 200 has been properly connected to the channel member 110, the step 506 of positioning the tip 200 to obtain an aliquot of liquid is performed by moving the tip 200 of the liquid handling apparatus 100 to the liquid sample 310. The liquid sample 310 may be contained in a vessel such as a well of a multiwell plate or a test tube. The liquid sample 310 is a target for the light 130 transmitted by the light transmitting device 120. Prior to positioning the tip 200 for aspiration, the method 500 includes the optional step 505 of ensuring that there is no residual liquid in the tip 200. With reference to FIG. 14, this may be achieved by transmitting light 130 from one or more light transmitting devices 121 positioned to transmit light within the tip 200. If there is residual liquid present in the tip 200, the pathway of transmitted light is changed and the change detected by the light detecting device 141. Upon receiving information of the detected change, the logic circuitry 160 may then instruct the display device 150 to report that residual liquid is present in the tip 200 according to any one or more of the variety of ways described hereinabove. If there is no residual liquid within the tip 200, no light is reflected to the light detecting device 141. Upon failing to detect light, the logic circuitry 160 may instruct the display device 150 to report that the tip 200 is clear and ready for aspiration.

Figure 13:
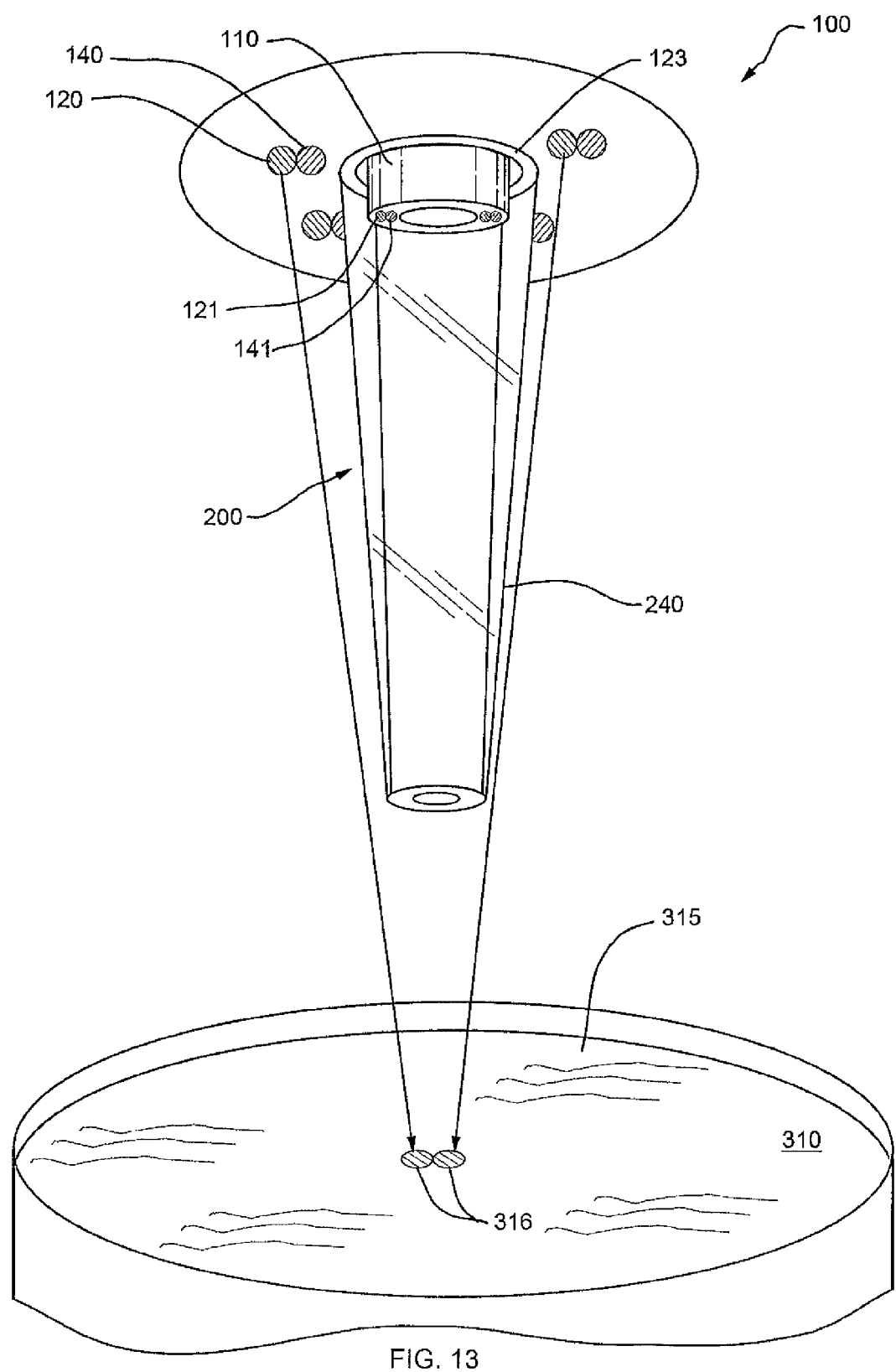
FIG. 13 is a side view of a first embodiment of the apparatus as it is being positioned to aspirate a liquid from a source.

The step 506 of positioning includes aligning the tip 200 properly over the sample 310. As shown in FIG. 13, that may be achieved by observing light marks 316 on the surface 315 of the sample 310. If the light marks 316 are not aligned, such as shown in the figure, then the tip 200 is not properly positioned. The step 506 also includes the step of properly immersing the tip 200 within the liquid sample 310. This may be performed automatically by the apparatus or manually by the operator. Initially, the tip 200 is held at some position, which may be arbitrarily chosen by the operator or an automated form of the liquid handling device 100, within the liquid sample 310 from which the aliquot is to be aspirated, as shown in FIG. 14. Light is then transmitted from the light transmitting device 120 to the surface 315 of the liquid sample 310. When the light 130 strikes the surface, the surface 315 becomes illuminated such that the light 130 acts as to spotlight at least a portion the surface 315. In this arrangement, a portion of the light 130 is reflected from the surface 315, and that light forms an understandable image, such as the solid circle mark 317 shown on the surface 315. The resolution of the circle mark 317 may be variable, such that it may become more focused as the tip 200 reaches the appropriate position above the surface 315 of the liquid sample 310. Alternatively, when multiple light transmitting devices 120 are used, it may be when all circles are aligned. The light transmitting device 120 may be configured to ensure that the circle mark 317 is properly focused when the tip 200 is in optimal immersion position for aspiration, such as shown in FIG. 14. In this arrangement, the operator can achieve the optimal immersion depth by manually adjusting the position of the tip 200 within sample 310 until the operator visualizes a single circle mark 317 having what is perceived to be optimal clarity or resolution. Alternatively, the optimal immersion position may be identified through automatic adjustment of the tip position by the liquid handling device 100 when the light detecting device 140 detects the intensity of the reflected light represented by the circle mark 317 and the logic circuitry 160 calculates that the circle marks 317 from all light transmitting devices 120 are aligned and/or in focus.

The next step of the method 500 of the present invention involves the step 508 of aspirating the liquid into the tip 200 after the determination has been made that the tip 200 has been immersed to the desired position. This step may be performed manually or automatically as is well known to those skilled in the art of liquid aspiration and dispensation. The method 500 may include the optional step 509 of ensuring that the liquid aliquot is contained in the tip 200. With reference to FIG. 14, this may be achieved by transmitting light 130 from one or more light transmitting devices 121 positioned to transmit light within the tip 200. When a liquid aliquot 330 is present in the tip 200, transmitted light 130 is reflected from surface 331 of the aliquot 330 and is detected by the light detecting device 141. Upon detecting the light 130, the light detecting device 141, via the logic circuitry 160, may then instruct the display device 150 and/or one or more of the light transmitting devices 121 to report that the aliquot 330 is present in the tip 200 according to any one or more of the variety of ways described hereinabove. If there is no aliquot 330 within the tip 200, no light 130 is reflected to the light detecting device 141. Upon failing to detect light 130, the light detecting device 141, via the logic circuitry 160, may instruct the display device 150 and/or one or more of the light transmitting devices 121 to report that the tip 200 does not contain the aliquot 330.

Upon determining that the tip 200 is properly connected to the channel member 110 and that the liquid aliquot is contained in the tip 200, the method 500 includes step 510 of dispensing the aliquot of liquid into a target vessel, which may be empty or which may include liquid sample 310. The tip 200 is positioned above the surface of the liquid sample 310 (or bottom of the vessel) for proper dispensing of the aliquot into the liquid sample 310. The tip 200 is initially held at a selectable position above the liquid sample 310 into which the aliquot is to be dispensed. Light 130 then is transmitted from the light transmitting device 120 to the surface 315 of the liquid sample 310 such that the surface 315 becomes illuminated. In this arrangement, a portion of the light 130 is reflected from the surface 315, which forms an image, such as circle mark 317 on the surface 315. Upon confirming that the circle mark 317 is singular and/or of desired intensity, it is determined that the tip 200 is held at the optimal distance above the surface 315 for aliquot dispensing. In this arrangement, the operator can achieve the optimal tip position above the target vessel by manually adjusting the position of the tip 200 with respect to the liquid surface 315 until the operator visualizes the circle mark 317 having maximum resolution. When it has been determined that the tip 200 is at the desired position, the aliquot within the tip 200 may be dispensed into the vessel.

In addition to assisting the operator to position the tip 200 at the preferred location for dispensing, there is an added benefit of employing the light transmitting device 120. Specifically, the transmitted light 130 allows the operator to better visualize the target. This enhanced visualization aids in the positioning of the tip 200. Furthermore, it is particularly advantageous that the light 130 is reflected near the tip 200 because the tip 200 normally has the focus of the operator's attention during use of the apparatus 10.

The step of positioning for aliquot dispensing may be performed manually as described above, or it may be performed automatically, such as part of an automated liquid handling process. In that process, the light detecting device 140 and the logic circuitry 160 operate together to detect the transmitted light, determine proper tip positioning and either report the information to an operator to complete the aliquot dispensing, or complete the dispensing step automatically. Those skilled in the art of liquid aliquot aspiration and dispensation will recognize the steps to be completed in dispensing the aliquot from the tip after confirming that the tip 200 is properly positioned for dispensation.

In an alternative arrangement of the present invention, the tip 200 may be configured with a modified region such that it glows, either by scattered light, or by the presence of some fluorescent material, when light is propagating inside the tip wall 240, and encounters this modified region. The angle that the light is propagating within the tip 200 is engineered so that Total Internal Reflection (TIR) is occurring with the tip 200 in air, but not when it is immersed in solution. When the tip 200 is in air, the glowing region "glows" because the light successfully propagates within the tip 200 to that point. However, when the tip 200 is immersed in solution, once the light reaches the solution region, it is no longer confined within the tip 200 because TIR no longer occurs. At this point the light exits the tip 200. Once the tip 200 has been immersed deep enough such that the glowing region is immersed, the light will escape the tip wall 240 before it has the chance to pass into the glowing region, and that region will "turn off" and no longer glow. There would then be, in effect, two regions of the tip 200, an upper and a lower. The object is to insert to the point that the lower region is off, but the upper region is on.

Other variations of the examples and designs described and shown herein can be implemented. For example, the steps of the method described may be performed in different order. Two or more steps may be performed simultaneously. Additionally, one or more steps of the method related to activation of the light transmitting device 120, the light detecting device 140, and/or the logic circuit 160 may be implemented as a computer program product as computer-readable signals on a computer-readable medium. For example, the computer-readable medium may be a non-volatile recording medium, an integrated circuit memory element, or a combination thereof. Such computer program product may include computer-readable signals tangibly embodied on the computer-readable medium, where such signals define instructions, for example, as part of one or more programs that, as a result of being executed by a computer, instruct the computer to perform one or more processes or acts described herein, and/or various examples, variations and combinations thereof. Such instructions may be written in any of a plurality of programming languages, for example, Java, Visual Basic, XML, C, or C++, Fortran, Pascal, Eiffel, Basic, COBOL, and the like, or any of a variety of combinations thereof. The computer-readable medium on which such instructions are stored may reside on one or more of a computer device and/or the components of a computer network system.

It is to be understood that various modifications may be made to the apparatus and method without departing from the spirit and scope of the invention.

What is claimed is:

1. A method for aspirating and dispensing liquids through a liquid holding tip from or to a target, the liquid holding tip forming a replaceable part of a liquid handling device, the method comprising the steps of:
   a. positioning the liquid holding tip with respect to the target, wherein the liquid holding tip includes a tip wall at least partially including a waveguide-quality material integral with or adjacent to the tip wall;
   b. transmitting at least one signal within the waveguide quality material to the target, wherein the at least one signal includes one or more indicia of position of the tip with respect to the target;
   c. detecting the at least one signal; and
   d. determining from the at least one detected signal one or more of: (1) whether the tip is properly attached to the liquid handling device; (2) whether the proper type of tip is connected to the liquid handling device; (3) whether the tip has contacted the surface of a liquid sample of the target, both when the tip is empty for aspiration and when the tip contains a liquid aliquot for dispensation; (4) whether the immersion depth of the tip in the liquid sample is acceptable; (5) whether the liquid aliquot is present in the tip; and (6) whether liquid is not present in the tip.

2. The method of claim 1 wherein the step of transmitting at least one signal includes the step of transmitting the at least one signal within air external to the tip.

3. The method of claim 1 wherein the step of transmitting the at least one signal includes the step of transmitting the at least one signal within air within the lumen of the tip.

4. The method of claim 1 wherein the at least one signal is a light signal, the method further comprising the steps of:
   a. reflecting the light from the target to form an image of variable resolution upon. the target; and
   b. moving the tip toward the target such that the resolution of the image becomes increasingly more focused as the tip approaches a desired position with respect to the target, wherein the image is substantially focused when the tip is substantially at the desired position with respect to the target and the image is not focused when the tip is not substantially at the desired position with respect to the target.

5. The method of claim 1 wherein the step of detecting the at least one signal includes the step or using one or more signal detecting devices arranged to detect at least one signal transmitted by the one or more signal transmitting devices.

6. The method of claim 1 wherein the method further includes the step of using logic circuitry coupled to the one or more signal detecting devices to interpret at least one detection signal received from the one or more signal detecting devices.

7. The method of claim 6 wherein the logic circuitry is programmed to control movement of the liquid handling device to adjust the position of the tip with respect to the target.

8. The method of claim 6 wherein the logic circuitry is programmed to indicate to a human operator to adjust the position of the with respect to the target, 9. A method for aspirating and dispensing liquids through a liquid holding tip from Or to a target, the liquid holding tip forming a replaceable part of a liquid handling device, the method comprising the steps of:
   a. positioning the tip with respect to the target;
   b. transmitting at least one signal to the target, wherein the at least one signal includes one or more indicia of position of the tip with respect to the target;
   c. detecting the at least one signal; and
   d. determining from the at least one detected signal one or more of: (1) whether the tip is properly attached to the liquid handling device; and (2) whether the proper type of tip is connected to the liquid handling device.

10. The method of claim 9 further comprising the step of determining from the at least one detected signal one or more of: (1) whether the tip has contacted the surface of a liquid sample of the target, both when the tip is empty for aspiration and when the tip contains a liquid aliquot for dispensation; (2) whether the immersion depth of the tip in the liquid sample is acceptable; (3) whether the liquid aliquot is present in the tip; and (4) whether liquid is not present in the tip.

11. The method of claim 9 wherein the step of transmitting at least one signal includes the step of transmitting the at least one signal within air external to the tip.

12. The method of claim 9 wherein the step of transmitting the at least one signal includes the step of transmitting the at least one signal within air within the lumen of the tip.

13. The method of claim 9 wherein the at least one signal is a light signal, the method further comprising the steps of:
   a reflecting the light from the target to form an image of variable resolution upon the target; and
   b. moving the tip toward the target such that the resolution of the image becomes increasingly more focused as the tip approaches a desired position with respect to the target, wherein the image is substantially focused when the tip is substantially at the desired position with respect to the target and the image is not focused when the tip is not substantially at the desired position with respect to the target.

14. The method of claim 9 wherein the step of detecting the at least one signal includes the step of using one or more signal detecting devices arranged to detect at least one signal transmitted by the one or more signal transmitting devices, 15. The method of claim 9 wherein the method further includes the step of using logic circuitry coupled to the one or more signal detecting devices to interpret at least one detection signal received from the one or more signal detecting devices.

16. The method of claim 15 wherein the logic circuitry is programmed to control movement of the liquid handling device to adjust the position of the tip who respect to the target.

17. The method of claim 15 wherein the logic circuitry is programmed to indicate to a human operator to adjust, the position of the tip with respect to the target.

* * * * *